United States Patent de Haan et al.

[11] Patent Number: 5,916,593
[45] Date of Patent: Jun. 29, 1999

[54] PROCESS OF MAKING DOSAGE UNITS BY WET GRANULATION

[75] Inventors: Pieter de Haan, Oss; Jocominus Antonius Maria Zwinkels, Nistelrode, both of Netherlands

[73] Assignee: Akzo Nobel, N.V., Arnhem, Netherlands

[21] Appl. No.: 08/793,976

[22] PCT Filed: Sep. 19, 1995

[86] PCT No.: PCT/EP95/03692

§ 371 Date: Sep. 16, 1997

§ 102(e) Date: Sep. 16, 1997

[87] PCT Pub. No.: WO96/09056

PCT Pub. Date: Mar. 28, 1996

[30] Foreign Application Priority Data

Sep. 22, 1994 [EP] European Pat. Off. .............. 94202728

[51] Int. Cl.$^6$ ................................ A61K 9/20; A61K 9/26
[52] U.S. Cl. .................. 424/465; 424/464; 424/470; 424/488; 424/489; 514/960; 514/841; 514/843
[58] Field of Search ...................................... 424/464, 465, 424/470, 489, 488; 514/960, 841, 843

[56] References Cited

U.S. PATENT DOCUMENTS

| | | |
|---|---|---|
| 3,969,502 | 7/1976 | Lachnit-Fixson . |
| 4,956,182 | 9/1990 | Bequette et al. . |
| 5,200,197 | 4/1993 | Wright et al. . |

FOREIGN PATENT DOCUMENTS

| | | |
|---|---|---|
| 0 491 443 | 6/1992 | European Pat. Off. . |
| 0491438 | 6/1992 | European Pat. Off. . |
| 0491443 | 6/1992 | European Pat. Off. . |
| 0503521 | 9/1992 | European Pat. Off. . |
| 0587047 | 3/1994 | European Pat. Off. . |
| 0613687 | 9/1994 | European Pat. Off. . |
| 9107173 | 5/1991 | WIPO . |
| 9418951 | 9/1994 | WIPO . |
| WO 94/18951 | 9/1994 | WIPO . |
| 9517168 | 6/1995 | WIPO . |

OTHER PUBLICATIONS

H.H. El–Shattawy, *Drug Dev. and Ind. Pharmacy,* 7:4:439–451, 1981.
Database WPI, Week 9502, M.W. Beasley et al.
H.H. El–Shattawy, Drug Dev. and Ind. Pharmacy, 7:439–451 1981.

Primary Examiner—Thurman K. Page
Assistant Examiner—Brian K. Seidleck
Attorney, Agent, or Firm—Mary E. Gormley

[57] ABSTRACT

The invention relates to a process of making pharmaceutical dosage units comprising at least desogestrel or Org 30659 (17α-17-hydroxy-11-methylene-19-norpregna-4,15-dien-20-yn-3-one), present in an amount of about 0.005 to 1.0 percent by weight of each pharmaceutical dosage unit, characterized in that the steroidal agent, and when required pharmaceutically acceptable excipients, are mixed with water and granulated.

15 Claims, No Drawings

PROCESS OF MAKING DOSAGE UNITS BY WET GRANULATION

The invention relates to a process of making dosage units comprising at least desogestrel or Org 30659 (17α-17-hydroxy-11-methylene-19-norpregna-4,15-dien-20-yn-3-one) present in an amount of about 0.005 to 1.0 percent by weight of each pharmaceutical dosage unit.

Methods for making tablets and other solid or dry pharmaceutical preparations are well-known. For example in the standard English language text Gennaro et al., Remington's Pharmaceutical Sciences, (18th ed., Mack Publishing Company, 1990, see especially Part 8: Pharmaceutical Preparations and Their Manufacture), methods of making tablets, capsules and pills and their respective components are described.

Three methods of making tablets include the wet-granulation, dry-granulation, and direct compression methods. Wet-granulation methods involve weighing out ingredients (including a solvent), mixing the ingredients, granulating them, screening them damp, drying them, dry screening, lubrication, and compressing the resultant admixture into tablets. Such procedures result in tablets having at least adequate tablet homogeneity. Wet-granulation methods may have a disadvantage when certain solvents, which may not be desired in view of environmental and safety concerns, are used.

An additional problem occurs in providing optimal tablet homogeneity when used with certain very potent medicinal compounds. For example, compounds such as certain extremely potent steroids require only very low doses of the compound per tablet (e.g. <1.0 milligrams (mg)/100 mg tablet) and do not always distribute entirely evenly throughout a tableting mixture possibly resulting in some tablets having relatively high amounts of steroid (i.e. "superpotent tablets"), while others have very low amounts of steroid or possibly none at all.

Very few solutions for these problems are offered, among which a dry-mix procedure as disclosed in European patent application 503,521.

The present invention offers a novel solution for obtaining tablets comprising low dosage of the micronised or finely milled steroidal progestogens desogestrel or Org 30659 with excellent content uniformity, by using a wet-granulation technique, in which the progestogen, and optionally pharmaceutically acceptable excipients, are mixed with water and granulated. The granulate obtained may optionally be mixed with pharmaceutically acceptable auxiliaries, and compressed into tablets.

The method is very suitable for tablets comprising the low dosage steroidal progestogens desogestrel or Org 30569, which are present in an amount of about 0.005 to 1.0, and preferably of about 0.01 to 0.5 percent by weight of each pharmaceutical dosage unit. Under desogestrel is also to understand its active metabolite 3-keto-desogestrel.

The progestogens desogestrel and Org 30659 can be admixed with estrogens selected from ethinyl estradiol (EE), estradiol, and mestranol. Usually mixtures of progestogens and estrogens are used. Most preferred are tablets comprising desogestrel and ethinyl estradiol.

Since tablets containing desogestrel (and also tablets containing Org 30659) are known to be unstable towards moisture, many attempts are done to exclude water in the manufacture process, for instance by using a dry-granulating method, or by using water-free organic solvents in wet-granulating methods. The marketed product (Marvelon®), for instance, is packed in a water impermeable sachet to prevent contact between the tablet and surrounding. Most remarkably it has now been found that the process of this invention, comprising granulation in an aqueous medium, provides a granulate of desogestrel or Org 30659 and ethinyl estradiol, from which tablets can be prepared which are much more stable towards moisture, than the previously aqueous-free prepared tablets.

Wet granulation distinguishes from dry granulation in that water or organic solvents are applied in wet granulation to produce agglomeration or granules.

The most widely used granulation methods in the pharmaceutical industry are the fluidized bed granulation and the wet-massing method in which a liquid is added to a powder or granulate in a vessel equipped with any type of agitation that will provide granules or agglomerates. Various operations can be recognised in the wet (massing) granulation, including milling of drugs and excipients, mixing of milled powders, preparation of binder solution, mixing the binder solution with the powder mixture to form the wet mass, coarse screening of wet mass, drying moist granules, screening dry granules, mixing the screened granules with lubricant and disintegrant, and finally filling the granulate into capsules or compressing the granulate to tablets. It is obvious that, depending on the selected excipients and the size of the batch and the selected equipment, some of the operations can be combined or are not required or particular operations can be included. General methods of preparing granules are for instance described in Pharmaceutical Dosage Forms: Tablets (Volume I). Ed. H. A. Lieberman, L. Lachman, J. B. Schwartz (1989), Marcel Dekker Inc. New York and Basel pp. 131–190.

Advantages of wet granulation include improvement of the cohesiveness and compressibility of powders, a good distribution and uniform content of micronised or finely milled low-dosage drugs, reduction of a great deal of dust and airborne contamination, prevention of segregation of components.

Small-scale production can be achieved by mixing and wetting the mass in mortars or stainless steel bowls, whereas for larger quantities twin-shell blenders, double-cone blenders, planetary mixers, rotary granulators, high shear mixers and fluid-bed granulation equipment can be applied. General mixing methods are disclosed in Pharmaceutical Dosage Forms (Volume 2). Ed. H. A. Lieberman, L. Lachman, J. B. Schwartz (1990), Marcel Dekker Inc. New York and Basel pp. 1–71. The dry excipients and the micronised or finely milled active ingredients are mixed in a suitable mixer, preferably a mixer in which both mixing and granulating can be performed, for instance a Gral high sheer mixer, after which an aqueous binder solution is added. Another preferred method is to suspending the active ingredients into the aqueous binder solution, which suspension is added to the dry mixture of excipients and granulated.

Granulates and tablets prepared by wet-granulation consist of several inert materials that can be found in conventional solid oral dosage forms in general. The ingredients can be classified in excipients which help to impart satisfactory processing and compression characteristics to the formulation like diluents, binders, glidants and lubricants and in excipients to give the desirable physical characteristics to the finished tablet like disintegrants and colors. If required the tablets can be provided with a film coat, for instance as disclosed in Pharmaceutical Dosage Forms (Volume 3). Ed. H. A. Lieberman, L. Lachman, J. B. Schwartz (1990), Marcel Dekker Inc. New York and Basel pp. 93–125.

Diluents (fillers) or bulking agents usually make up the major portion of the tablet. The group of most commonly used diluents include the water insoluble calcium phosphates (di- and tribasic), calcium sulfate dihydrate, calcium carbonate, starch, modified starches and microcrystalline cellulose and the water soluble lactose, sucrose, dextrose, mannitol and sorbitol.

The substances that bind powders together and provide cohesiveness to the tablet formulation are binding agents or adhesives. Binders can be added dry and blended with the diluents and the drug. In this case binders are activated by addition of water or other solvents. In other manufacturing procedures, the adhesives are dissolved or slurried in a liquid and, in this form, added to the mixed powders. Conventional binders include gelatin, water soluble modified starch, and sugars as sucrose, glucose, dextrose, molasses and lactose. Natural and synthetic gums which have been used include tragacanth, magnesium aluminium silicate, acacia, ammonium calcium alginate, sodium alginate, carboxymethylcellulose, hydroxypropylcellulose, methylcellulose, hydroxypropylmethylcellulose, polyvinylpyrrolidone, polyethylene glycol and clays like Veegum. Depending on for example the solubility of the binders in the various liquids, the binder can be added to the powder mix as a solution in water, a water-solvent mixture and in a organic solvent.

Materials to improve the flow characteristics are referred to as glidants. As an example, silicon dioxide, magnesium lauryl sulfate, magnesium aluminium silicate, magnesium oxide, talc or clays can be incorporated into the formulation to reduce interparticulate friction and to eliminate the problems associated with the flow of materials from larger to smaller apertures in the tablet presses.

Before filling capsules or sachets, or compressing tablets, lubricants are mostly added to prevent friction and wear during processing. Some of the lubricants also demonstrate anti-adherent properties that can be relevant in case of sticking of tablet granulations to the faces of the punches and the die walls. Examples of the group of lubricants are the metallic stearates (magnesium stearate), talcum, stearic acid, sodium stearyl fumarate, hydrogenated vegetable oil, high melting point waxes, and corn starch.

A component incorporated into the tablets to help the tablet to break up and dissolve to release the active component is the disintegrant. The total amount of disintegrant can be added to the granulation just prior to compression, can be added to the total mass of powdered materials before the wet granulation process takes place or can be simply divided into one portion added before wet granulation and one portion added dry to the granulates. Examples of the group of disintegrants that can be applied are starch (Starch 1500), microcrystalline cellulose (Avicel PH 101 and Avicel PH 102), purified wood cellulose, alginic acid, sodium starch glycolate, guar gum, cross carmellose sodium, crosslinked polyvinylpyrrolidone and ion exchange resins.

The tablets obtained by the process of this invention are free from organic solvents, and comprise a progestogen selected from desogestrel and Org 30659, present in an amount of about 0.005 to 1.0 percent by weight of each pharmaceutical dosage unit, a small amount being less than 20% (e.g. 0.5–20%), and preferably less than 10% by weight of water, and optionally an estrogen. Preferably the progestogen is desogestrel and the estrogen is ethinyl estradiol. The amount of water can vary and depends from the drying conditions applied. The tablets, however, always possess trace amounts of water, usually less than 10% by weight, and preferably about 0.5 to 10% by weight.

The invention is further illustrated by the following examples.

EXAMPLE I

The active ingredients were processed to a homogeneous granulation comprising (per tablet):

| | | |
|---|---|---|
| desogestrel (micronised) | | 150 µg |
| EE (micronised) | | 30 µg |
| hydroxypropylcellulose | | 1.95 mg |
| corn starch | | 6.50 mg |
| colloidal silicon dioxide | | 0.98 mg |
| magnesium stearate | | 0.33 mg |
| lactose | to | 65 mg |

For a 1 kg batch a Gral 10 high shear mixer was filled with lactose 200M and corn starch. After mixing for 1 min a dispersion of desogestrel and EE (ethinyl estradiol) in an aqueous granulation solution of hydroxypropylcellulose (125 ml) was added quantitatively to the mass. Then 25 ml of water was used to rinse the beaker and subsequently added to the mixture. The mixture was granulated with the Gral 10 for 2.5 minutes. The obtained wetted mass was dried for 4 h in a Marius vacuum cabinet under diminished pressure at 40° C. After drying and screening through a 710 µm sieve with an Erweka apparatus the granulate was admixed with colloidal silicon dioxide and magnesium stearate. The granulate was compressed to tablets.

EXAMPLE II

A granulate with the composition in Example I was manufactured. The granulation was performed with ethanol instead of water in the binder solution.

EXAMPLE III

Tablets from Example I and Example II were subjected to storage at 40° C. for two months at relative humidities (RH) of 10 and 95% respectively. The decomposition of desogestrel was calculated.

| | Decomposition (%) | |
|---|---|---|
| | 10% RH | 95% RH |
| Tablets Example II | 1 | 4 |
| Tablets Example I | 0 | 1 |

Tablets prepared without aqueous binder solution show susceptibility to humidity upon storage (Example II), whereas tablets prepared with an aqueous binder solution show less susceptibility to humidity and an improved stability (Example I).

EXAMPLE IV

The active ingredients were processed to a homogeneous granulation comprising:

| | |
|---|---|
| Org 30659 (finely milled) | 60 µg |
| hydroxypropylcellulose | 1.95 mg |
| corn starch | 6.50 mg |
| magnesium stearate | 0.325 mg |
| lactose | 56.165 mg |

For a 1 kg batch a Gral 10 high shear mixer was filled with lactose 200M and corn starch. After mixing for 1 min a dispersion of Org 30659 (17α-17-hydroxy-11-methylene-19-norpregna-4,15-dien-20-yn-3-one) in an aqueous granulation solution of hydroxypropylcellulose (125 ml) was added quantitatively to the mass. Then 25 ml of water was used to rinse the beaker and subsequently added to the mixture. The mixture was granulated with the Gral 10 for 2.5 minutes. The obtained wetted mass was dried for 4 h in a Marius vacuum cabinet under diminished pressure at 40° C. After drying and screening through a 710 μm sieve with an Erweka apparatus the granulate was admixed with magnesium stearate. The granulate was compressed to tablets.

EXAMPLE V

A granulate with the composition in Example IV was manufactured. The granulation was performed with ethanol instead of water in the binder solution.

EXAMPLE VI

Tablets from Example IV and Example V were subjected to storage at 30° C. for one month at relative humidities (RH) of 10 and 95% respectively in open glass containers. The decomposition of Org 30659 was calculated.

|  | Decomposition (%) | |
| --- | --- | --- |
|  | 10% RH | 95% RH |
| Tablets Example V | 0 | 6 |
| Tablets Example IV | 0 | 0 |

Tablets prepared without aqueous binder solution show susceptibility to humidity upon storage (Example V), whereas tablets prepared with an aqueous binder solution show less susceptibility to humidity and an improved stability (Example IV).

EXAMPLE VII

The active ingredients were processed to a homogeneous granulation comprising (per tablet):

| desogestrel (micronised) | | 150 μg |
| --- | --- | --- |
| EE (micronised) | | 30 μg |
| hydroxypropylcellulose | | 1.95 mg |
| corn starch | | 6.50 mg |
| colloidal silicon dioxide | | 0.98 mg |
| magnesium stearate | | 0.33 mg |
| lactose | to | 65 mg |

For a 1 kg batch a Gral 10 high shear mixer was filled with lactose 200M, corn starch, desogestrel and EE (ethinyl estradiol). After mixing for 1 min an aqueous granulation solution of hydroxypropylcellulose (125 ml) was added quantitatively to the mass. Then 25 ml of water was used to rinse the beaker and subsequently added to the mixture. The mixture was granulated with the Gral 10 for 2.5 minutes.

The obtained wetted mass was dried for 4 h in a Marius vacuum cabinet under diminished pressure at 40° C. After drying and screening through a 710 μm sieve with an Erweka apparatus the granulate was admixed with colloidal silicon dioxide and magnesium stearate. The granulate was compressed to tablets.

EXAMPLE VIII

The active ingredients were processed to a homogeneous granulation comprising:

| Org 30659 (finely milled) | | 60 μg |
| --- | --- | --- |
| polyvinylpyrrolidone | | 1.95 mg |
| corn starch | | 6.50 mg |
| magnesium stearate | | 0.325 mg |
| lactose | to | 65 mg | and granulated and compresses into tablets according to the method of Example IV.

EXAMPLE IX (COMPARISON EXAMPLE)

A granulate having the composition of Example VIII was manufactured using acetone instead of water. The tablets obtained therefrom were stored for 12 months at 75% relative humidity at 30° C. and 40° C. in open glass containers. The tablets of Example VIII were stored under the same conditions and the content in percentage of the initial content at zero time was calculated:

|  | 30° C. | 40° C. |
| --- | --- | --- |
| Tablets Example VIII | 94.4% | 73.6% |
| Tablets Example IX | 64.1% | 44.5% |

EXAMPLE XI

Tablets were prepared comprising:

| Org 30569 (micronised) | | 7.5 μg |
| --- | --- | --- |
| estradiol | | 2 mg |
| hydroxypropylcellulose | | 1.95 mg |
| corn starch | | 30% |
| colloidal silicon dioxide | | 0.98 mg |
| magnesium stearate | | 0.325 mg |
| lactose | to | 65 mg |

Granulation was performed according to Example IV using 280 ml of granulation liquid to obtain granulates. Tablets were compressed on a rotary press.

We claim:

1. A process of making pharmaceutical dosage units units comprising at least one steroidal progestogen selected from the group consisting of desogestrel and 17α-17-hydroxy-11-methylene-19-norpregna-4.15-dien-20-yn-3-one, present in an amount of about 0.005 to 1.0 percent by weight of each pharmaceutical dosage unit, comprising mixing the progestogen with pharmaceutically acceptable excipients and water and granulating the mixture.

2. The process according to claim 1, wherein the resulting granulate is compressed into tablets.

3. The process according to claim 1, wherein the progestogen is present in an amount of about 0.01 to 0.5 percent by weight of each pharmaceutical dosage unit.

4. The process according to claim 1, wherein the progestogen is admixed with an estrogen.

5. The process according to claim 1, wherein the progestogen is desogestrel.

6. A tablet free from organic solvents, comprising a progestogen selected from desogestrel and Org 30659, present in an amount of about 0.005 to 1.0 percent by weight of each pharmaceutical dosage unit, and less than 20% by weight of water.

7. The tablet of claim 6, wherein the progestogen is desogestrel.

8. The process of claim 1, wherein the resulting granulate is compressed into tablets.

9. The process of claim 1, wherein the amount of progestogen is about 0.01 to 0.5 percent by weight of each pharmaceutical dosage unit.

10. The process of claim 9, wherein the progestogen is admixed with an estrogen.

11. The process of claim 9, wherein the progestogen is desogestrel.

12. The process of claim 10, wherein the estrogen is ethinyl estradiol.

13. The process of claim 4, wherein the estrogen is ethinyl estradiol.

14. The table of claim 6, further comprising an estrogen.

15. The tablet of claim 14, wherein the estrogen is ethinyl estradiol.

* * * * *